United States Patent [19]
McCoy

[11] Patent Number: 5,487,772
[45] Date of Patent: Jan. 30, 1996

[54] CARBOXYLATE NUTRIENTS AND METHODS FOR THEIR PRODUCTION AND USE

[76] Inventor: Paul E. McCoy, 255 Dolphin Point Rd., Unit 511, Clearwater, Fla. 34630

[21] Appl. No.: 371,352

[22] Filed: Jan. 11, 1995

Related U.S. Application Data

[63] Continuation-in-part of Ser. No. 182,218, Jan. 14, 1994, abandoned, which is a continuation-in-part of Ser. No. 146,958, Nov. 3, 1993, Pat. No. 5,453,277, and a continuation-in-part of Ser. No. 776, Jan. 5, 1993, abandoned.

[51] Int. Cl.$^6$ .............................. A23K 1/175; C05F 5/00
[52] U.S. Cl. .................. 71/26; 426/74; 426/807
[58] Field of Search ................... 426/74, 285, 304, 426/807, 455, 456

[56] References Cited

U.S. PATENT DOCUMENTS 3,353,949 11/1967 Nau ............................................ 426/26
3,567,460 3/1971 McCoy .................................... 426/635

*Primary Examiner*—Helen Pratt
*Attorney, Agent, or Firm*—Herbert W. Larson

[57] ABSTRACT

Soil dispersible and water dispersible granular nutrients for use in fertilizers or animal feeds include granules having a crystallized saccharide binder with carboxylates (sucrates) of a nutrient embedded therein, A method of preparing the nutrients containing granules is provided, A reducible nutrient compound is converted to a nutrient carboxylate (sucrate) by reacting the reducible nutrient with a sprayed stream of a stoichiometric excess of reducing saccharides (sugar cane molasses) containing at least 76% by weight solids at a temperature of 160° to 175° F.

11 Claims, 2 Drawing Sheets

CARBOXYLATE NUTRIENTS AND METHODS FOR THEIR PRODUCTION AND USE

PRIOR APPLICATION

This application is a continuation-in-part of application Ser. No. 08/182,218 filed Jan. 14, 1994, which is a continuation-in-part of 08/146,958 filed Nov. 3, 1993, now U.S. Pat. No. 5,453,277 and application Ser. No. 08/000776, filed Jan. 05, 1993, now abandoned.

BACKGROUND OF THE INVENTION

1. Field of The Invention

The present invention relates to soil dispersible, water dispersible granular nutrient and to methods for making and using such granular nutrients. More particularly, the present invention relates to granules having such nutrients embedded within a saccharide binder.

2. Description of the Prior Art

Numerous tests and many years of experience of the agriculture industry of the United States have demonstrated the need for certain nutrients for plant and animal growth. Some are more difficult than others to supply in a form which is easily taken up. In soil, there is the further problem of maintaining the nutrients in position over time.

U.S. Pat. No. 3,567,460 relates to the use of soil dispersible and water dispersible plant and animal nutrient compounds in a granular form comprising nutrient particles selected from the group made up of metallic oxides, metallic sulphates, metallic oxysulphates and metallic oxsulphates placed within a water-soluble saccharide binder.

U.S. Pat. No. Reissue 32,909 relates to the use of metal oxycarboxylates as suppliers of metal nutrients to plants, animals and humans.

U.S. Pat. No. 4,589,906 relates to the use of various divalent and trivalent metals in organic carboxylate form as starting materials for the formulation of plant fertilizers.

Prior art nutrient compounds generally suffer from disadvantages in speed and effectiveness of uptake of the nutrients. Therefore, there is a need for granular nutrient products which make the nutrients in the granules more available for plant uptake. It is an object of the present invention to provide such products.

SUMMARY OF THE INVENTION

Accordingly, the present invention is directed toward providing granular plant nutrient compounds. Nutrient compounds of the present invention are formed by agglomerating or otherwise binding the fines into a granule whose outer coating is a water soluble material. During the process of the agglomeration, the nutrient fines undergo a chemical reaction with the binder whereby carboxylated nutrients are produced as the end product. By utilizing the teachings of the invention, a certain amount of gas such as carbon dioxide is entrapped in the granule. When the outer coating dissolves in the presence of moisture, the expanding volume of the gas explodes the granule and aids in dispersing the carboxylated nutrients throughout the medium surrounding the original granule.

In one aspect, the invention provides a nutrient product comprising a plurality of nutrient-containing granules prepared by the steps of:

(A) introducing a finely divided powdered oxide of a reducible nutrient-containing compound into a mixer and spraying on the powdered oxide a saccharide binder having at least 76% by weight solids content, the binder having a stoichiometric excess of reducing saccharides relative to said reducible nutrient-containing compound, and mixing said binder and powdered oxide to form granules having said particles embedded within said binder wherein the reducing saccharides react with said reducible nutrient compound to form carboxylates (sucrates) of said nutrient;

(B) drying said granules by application of heat between 160° 175° F.; and (C) curing said granules for a sufficient time period to permit substantial termination of exothermic carboxylate-forming (sucrate-forming) reactions.

In another aspect, the invention provides a soil dispersible and water dispersible granular nutrient for use in fertilizers or animal feeds, said nutrient including granules comprised of a crystallized saccharide binder having carboxylates (sucrates) of a nutrient embedded therein.

In another aspect, the invention provides a method of supplying nutrients to a plant or animal comprising administering to said plant or animal an effective amount of a granular nutrient having granules comprised of a crystallized saccharide binder, and embedded within said binder, carboxylates (sucrates) of a nutrient.

In another aspect, the invention provides a fertilizer or animal feed containing, in addition to nutrients essential to growth or life, a granular nutrient having granules comprised of a crystallized saccharide binder, and embedded within said binder, carboxylates (sucrates) of a nutrient.

In another aspect, the invention provides a method of producing a granular nutrient comprising the step of converting a reducible nutrient compound to a nutrient carboxylate (sucrate) by reacting said reducible nutrient compound with a stoichiometric excess of reducing saccharides.

Other features and advantages of the present invention will become apparent from the following description of the invention which refers to the accompanying drawings.

For the purpose of illustrating the invention, there is shown in the drawings an embodiment which is presently preferred; it being understood, however, that the invention is not limited to the precise arrangements and instrumentalities shown.

DETAILED DESCRIPTION OF THE INVENTION

Preferred nutrients which may be provided in accordance with the invention include major primary nutrients without which life cannot be sustained (e.g., phosphate and potassium) and secondary nutrients required in some quantities for growth and nutrients which, even if not necessary to sustain life, will further improve plant and/or animal growth and health. These nutrients are well known in the art. Among the nutrients which may be supplied in accordance with the invention are cationic nutrients such as manganese, zinc, copper, iron, calcium, potassium, magnesium, boron, cobalt, molybdenum, lithium, yttrium, thorium and rare earth elements. Cationic metals are especially useful in accordance with the invention.

The invention utilizes, as starting compounds, a reactant binder and reducible compounds which include desired nutrients in the form of oxides, sulfates and other reducible compounds and salts. The reducible compounds are reduced in the presence of reducing sugars in the binder, (i.e., monosaccharides and aldehyde-functional disaccharides) and form carboxylates (sucrates) of said nutrient. For example, when a cationic metal nutrient compound such as a metal oxide is reacted with reducing sugars, the desired metal carboxylate (sucrate) products are formed in an exothermic reaction. A stoichiometric excess of reducing sugars sprayed onto a finely divided powdered oxide is preferred because it is desirable to create as much carboxylate (sucrate) product as possible while leaving behind only a small amount of unreacted reducible nutrient compounds. Preferably the ratio of product carboxylate (sucrate) to unreacted starting nutrient compounds should be at least 1:1, preferably 3:1 and more preferably, in excess of 9:1. It is believed that the uptake of product carboxylate (sucrate) is greatly improved relative to the starting compounds such as metal oxides.

Suitable starting compounds include, but are not limited to various oxides of manganese, zinc, copper, iron and magnesium (e.g., MnO, $Fe_2O_3$ and FeO). Mixtures of the compounds may also be used, for example, mixtures of iron and manganese compounds in a ratio between about 1.5:1 and 2.0:1 by weight.

Figure 1:
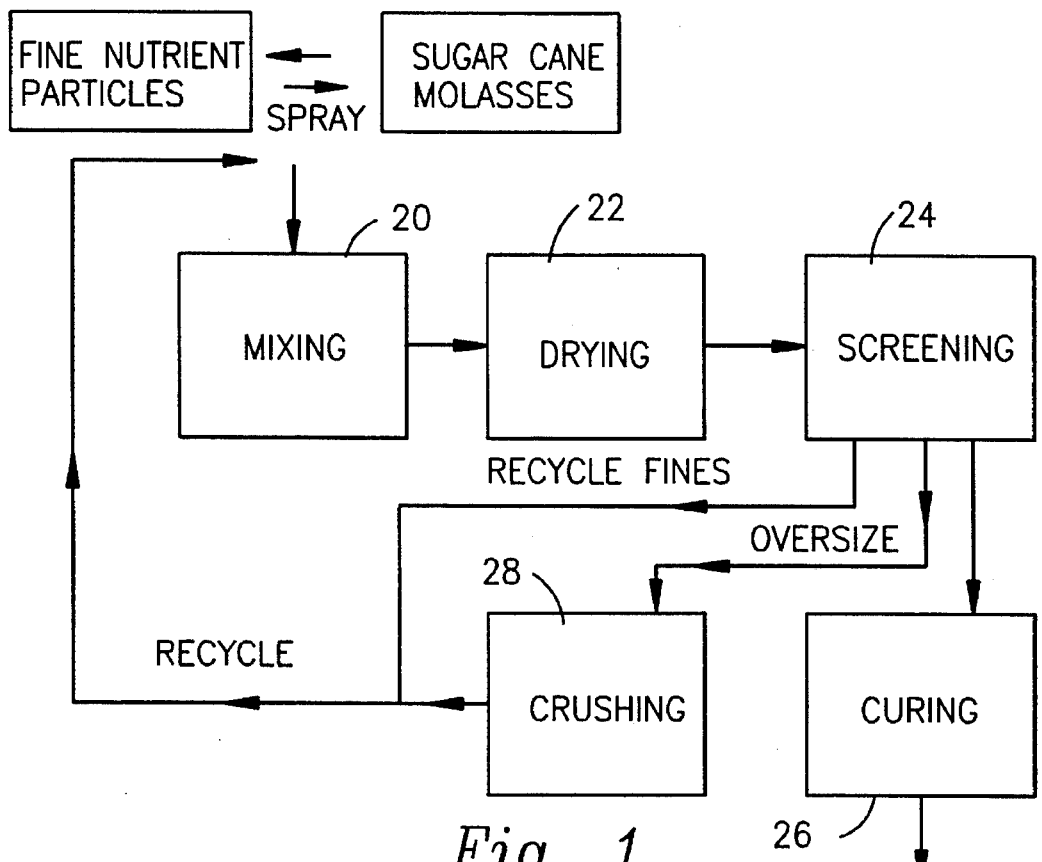
FIG. 1 is a schematic drawing showing the process steps of one preferred manufacturing process in accordance with the invention.

Referring to FIG. 1, the reducible starting compounds are preferably formulated as fine particles (e.g., about 44 microns or smaller) and are introduced into a mixer 20 as a powder countercurrent to a spray of the binder which contains at least 76% by weight solids. The binder crosses the stream of reducible starting oxide compound allowing the binder and starting oxide compounds to meet. The binder provides the reducing sugars which react with the starting compounds to form carboxylates (sucrates), and also provides the saccharides which preferably form a crystalline shell about the carboxylates (sucrates) that are formed.

The starting materials and binder, after making contact, fall into the mixer 20. A mixer which can be utilized, for example, is a drum open at one end having a diameter of about 48 inches and an interior length of about 30 inches. The drum is angled so that its open end is above its closed end, and the drum is rotated about its cylindrical axis. As the drum is rotated, granules of the binder are formed having embedded therein a combination of starting compounds and product carboxylates (sucrates). It should be noted that some of each is expected because the conversion of starting material to carboxylate (sucrate) begins at initial contact but is not completed until a later curing step described below.

The granules grow in size as additional binder is continually coated about the outer surface of the granule in the mixer. Time in the mixer preferably varies between about 1 minute and 5 minutes depending upon the size of granule desired. For a granule of −6 +16 mesh size (U.S. standard sieve) about 3 to 5 minutes is appropriate. For granules of −10+20 mesh size, 1–2 minutes may be sufficient.

Preferably the starting compound and binder combine to form a very fine granule in the cross spray described above, then fall to the bottom of the mixer and are gradually displaced forward as they grow, until they reach the desired granule size and fall out the open end. Depending upon the desired granule size, rate of introduction of starting components may be adjusted to cause the particles to progress at a rate which leaves them in the mixer for the desired time period. In accordance with the invention, no granulator is required between the mixing step and a subsequent drying step 22.

The binder and starting nutrient compound may also be introduced with a screw conveyer which has the additional advantage of helping control granule size. Because of the heat created by the ongoing exothermic reaction, drying begins also.

The saccharide binder is preferably a mixture of large and small polysaccharides containing at least 76% solids with a minimum hydrometer brix of 82, which includes a high concentration of reducing sugars for participation in the reaction. Hydrometer brix was first derived for pure solutions of sucrose and relates the specific gravity of a sucrose solution to its total sucrose content. In the case of pure sucrose the degrees brix is equivalent to the total sucrose content and also the total solids content on a weight/weight basis.

In one preferred embodiment of the invention, the binder is a mixture consisting essentially of cane sugar molasses and water, wherein the water is present in a concentration of 25% (by weight based on weight of the cane sugar molasses and water combination), and more preferably 35% to 50% water (e.g., a mixture of 60% cane sugar molasses and 40% water). The high concentration of water breaks down higher polysaccharides into both reducing monosaccharides and also aldehyde-containing disaccharides. Together with the reducible starting compound, these saccharides react to form carboxylates in accordance with the reactions set forth below. The resulting nutrient carboxylate is more available for uptake than the starting nutrient compounds (e.g., oxides). A typical product of the reaction is thus a carboxylate of a cationic nutrient having the formula:

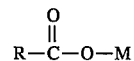

wherein M is the nutrient cation from the group manganese, zinc, copper, iron, magnesium, boron, calcium or potassium and R is the saccharide residue, i.e., the remaining portion of the saccharide molecule other than its aldehyde group which has been converted to the carboxylate group. Cane sugar molasses is the preferred choice for providing the R saccharide residue.

One side product of the reaction, especially where dioxides such as $MnO_2$ are present in small amounts in the starting material, is an oxidized carbohydrate which further breaks down to yield carbon dioxide gas which can be trapped in the growing granule and which, during use, acts to disperse the active nutrients as the polysaccharide binder dissolves.

Without intending to be bound by theory, it is believed that amorphous polysaccharides break down to the aldehyde forms of disaccharides and monosaccharides and indeed to such sugars (carbohydrates) as d-glucose, d-mannose, d-fructose, etc.

Such reducing sugars have the general aldehyde structure:

$$R-\overset{\overset{O}{\|}}{C}-H$$

With water and heat (energy), polysaccharides are hydrolyzed to disaccharides and then to monosaccharides. Plants do this with photosynthesis and actually secrete carboxyl groups to take up nutrients in ion exchange reactions.

Monosaccharides also undergo hydrolysis with water to convert from the aldehyde form to the carboxylate ion $$\left[ R-\overset{\overset{O}{\|}}{C}-O \right]^-$$

and $$R-\overset{\overset{O}{\|}}{C}-OH$$

In the presence of some cations, notably Zn and Fe, even in the forms of ZnO, FeO and $Fe_2O_3$, the reaction potential is greater to form a zinc or iron carboxylate $$\left[ R-\overset{\overset{O}{\|}}{C}-OZn \right]^+, \left[ R-\overset{\overset{O}{\|}}{C}-OFe \right]^+$$

rather than the weak acid $$R-\overset{\overset{O}{\|}}{C}-OH.$$

As can be seen from the above ion formations, the monosaccharide is actually oxidized by reducing the cation oxide. Indeed, this is to be expected since monosaccharides are reducing agents and act as such in the process.

Manganese (Mn) acts somewhat differently in that the x-ray diffraction patterns show that the $Mn^{++}$ ion "pops" in and out of the carboxylate structure.

It is known that the carbonyl group, i.e., $$\overset{O^-}{\underset{/\ \backslash}{\overset{\|}{{}^+C}}},$$

is electron withdrawing and that in the carbonyl group, the carbon is partially positive and the oxygen is partially negative. It is also known that manganese has seven different valence states and goes up and down the scale at will. Its most stable form is $Mn^{++++}$, although if kept in a reduced state, $Mn^{++}$ is stable.

It therefore follows that in the above process, the resultant manganese compound oscillates between $$\left[ R-\overset{\overset{O}{\|}}{C}-OMn \right]^+ \quad (a)$$

and $$\left[ R-\overset{\overset{O:Mn}{\ }}{C}-OH \right]^+. \quad (b)$$

In either case, the total reaction can be represented as:

$$R-\overset{\overset{O}{\|}}{C}-H + H_2O \longrightarrow R-\overset{\overset{O}{\|}}{C}-OH + 2H^+ \text{ (weak acid)} \quad (1)$$

$$R-\overset{\overset{O}{\|}}{C}-OH + MnO + H_2 \longrightarrow \left[ R-\overset{\overset{O}{\|}}{C}-OMn \right]^+ + H_2O + [OH]^- \quad (2)$$

and similarly for zinc and iron.

In the case of (b) above, the reactions are:

$$R-\overset{\overset{O}{\|}}{C}-H + H_2O \longrightarrow R-\overset{\overset{O}{\|}}{C}-OH + 2H^+ \text{ (weak acid)} \quad (1)$$

$$R-\overset{\overset{O}{\|}}{C}-OH + MnO + H_2 \longrightarrow \left[ R-\overset{\overset{O:Mn}{\ }}{C}-OH \right]^+ + 2[OH]^- \quad (2)$$

And indeed, the water dispersion of the granular nutrient materials tests mildly alkaline, as would be expected.

In order to achieve these carboxylates (sucrates), it has now been found necessary to use excess reducing saccharides in the manufacturing process. This assures a more than ample supply of reducing sugars, carbonyl groups and carboxyl groups, not only to achieve the desired ionization but to keep the oxygen seeking cations in the reduced state.

Referring now to the drawings wherein like numerals indicate like elements, there is shown in FIG. 1 a mixing step 20 which may advantageously be carried out in a mixer as described above. The nutrient compounds (e.g. MnO) and the binder are mixed by cross-spraying them above the opening to the mixer. The mixture of the nutrient particles and the binder then enters the mixer through a raised end of the mixer.

The binder comprises a water soluble polysaccharide and/or a monosaccharide, such as the aldehyde forms of sugars, d-glucose (aldehyde form), d-mannose, d-fructose, osone, maltose, molasses, molasses extract, or cane sugar extract mixed with water. For example, 15 gallons of cane sugar molasses (176 lbs. wet weight or 134 lbs. dry weight) with 10 gallons of water (83 lbs. $H_2O$) may be used. Molasses often contains at least 48% sugars (carbohydrates: monosaccharides, disaccharides and polysaccharides) with from 12% to 16% sucrose. A preferred binder is 60% molasses and 40% water (w/w).

The mixer is rotated so that the nutrient particles and the binder are mixed. The type of nutrient used and the size of the granules desired determine the processing time in the mixer. Broadly, longer times will produce coarser granules.

By way of illustration but without limitation of the scope of the invention, following are some examples of the process parameters of the invention.

Typical formulations for Mn, Zn and Fe are:

Mn 1836 lbs. MnO, 43% Mn
  134 lbs. dry wt. binder (176 lbs. wet + water)
    30 lbs. final moisture (1.5%)

2000 lbs.
Zinc, 36% Zn 1714 lbs. Zinc Oxide, 42% Zn
  122 lbs. Lime (filler)
  134 lbs. Binder (dry wt. or 176 lbs. wet + water)

|   |   |
|---|---|
| 30 lbs. | Final Moisture (1.5%) |
| 2000 lbs. | |

| | |
|---|---|
| 2000 lbs. Iron, 50% Fe | |
| 1613 lbs. | Iron Oxide, 62% Fe |
| 223 lbs. | Lime (filler) |
| 134 lbs. | Binder (dry wt. or 176 lbs. wet + water) |
| 30 lbs. | Final Moisture (1.5%) |
| 2000 lbs. | |

All above weights and measures are given in terms of per net ton of final product.

Figure 3:
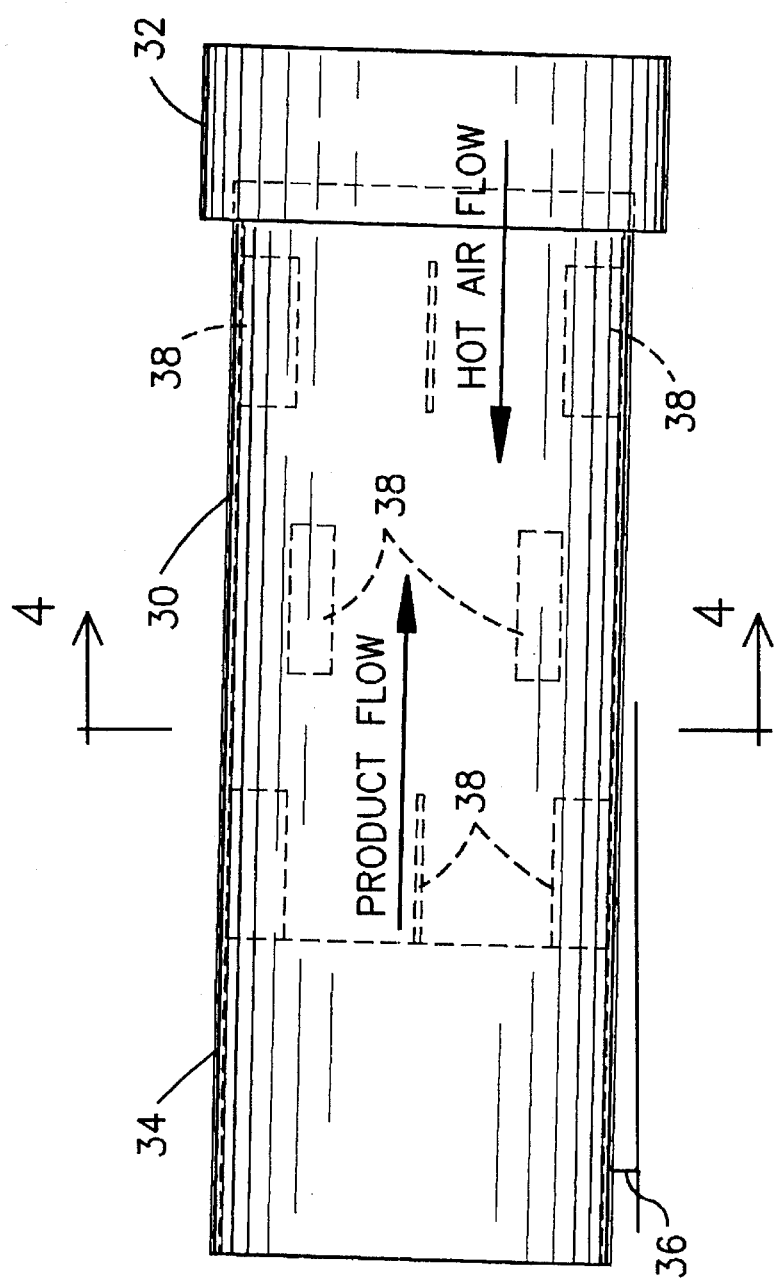
FIG. 3 is a side elevation view of the rotary dryer used in the manufacturing process.
Figure 4:
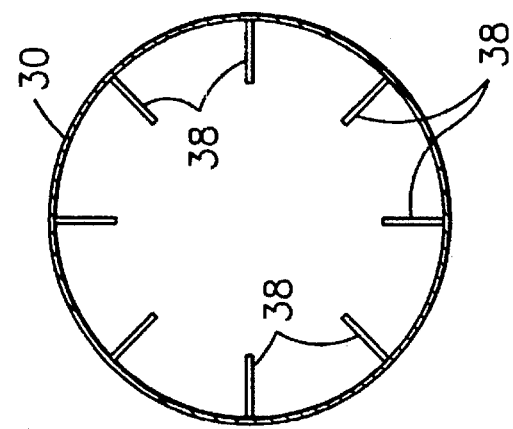
FIG. 4 is an end view of the rotary dryer.

The output of mixer, in granular form, is fed to a rotary dryer 20. (Drying step 22 is carried out in the dryer.) A modified rotary dryer 30, should be used as shown in FIGS. 3–4. A preferred drying unit allows progression of the granules from a "cold" end to a hot end thereof. See FIGS. 3–4. (It should be noted that even the cold end is well above ambient temperature.) Such a drying unit may include a heat source 32 at its hot end of a forty foot circular dryer about five feet in diameter and a counter current air flow moving in a direction opposite to the motion of the granules (i.e., away from the hot end 32 and toward the cold end 34). The air naturally cools as it travels toward the cold end and away from the heat source. The temperature range at the hot end is preferably from 160° F.–175° F. Temperatures above 180° F. are undesirable since it tends to drive the chemical reaction back to oxides from the desirable carboxylates (sucrates) and burn the molasses. At 175° F. the granules should remain in the dryer about 15–20 minutes and at 160° F. about 25 to 30 minutes.

The moisture content of the material being fed to the dryer is preferably between 5% and 20% depending upon the desired size of the final granules and their desired porosity. Typical granules have a dryer input moisture content of 10% to 12% and a dryer output moisture content of 1% to 5%. The dryer should have a slight angle of inclination 36 at its cold end and fins or flights 38 to lift and tumble the granules.

From drying step 22, the material is fed to screening step 24. At this step, where granules (–8 +20 for example) are to be shipped, all granules larger than 8 mesh are fed to crushing step 28 where any standard crusher (i.e., a rolls crusher) is used to pulverize the oversize granules. All granules smaller than mesh 20 (considered to be fines for this purpose) are also screened out. Both the fines and the pulverized coarse granules are recycled back to the mixer and reprocessed by the method of the invention.

The proper size granules are preferably then cured in the curing step 26 for a sufficient time period to permit substantial termination of exothermic carboxylate-forming reactions. Preferably the product is cured until it has returned to ambient temperature, and preferably for at least 12 to 24 hours thereafter. Subsequently, the product may be fed to a packaging step as required, or formulated as a component into other nutrient-containing products.

To obtain the desirable nutrient carboxylates of this invention, the ratio of dry weight cane sugar molasses to cation carrier dry weight employed is as follows:

| Parts Molasses | 100 Parts Cation | = | Sucrate Product |
|---|---|---|---|
| 11 | $M_nO$ (50% Mn) | = | Manganese sucrate |
| 10 | Zn O | = | zinc sucrate |
| 13 | $Fe_3O_4$ | = | iron sucrate |

| Parts Molasses | 100 Parts Cation | = | Sucrate Product |
|---|---|---|---|
| 10 | MgO or $Mg(OH)_2$ | = | magnesium sucrate |

Figure 2:
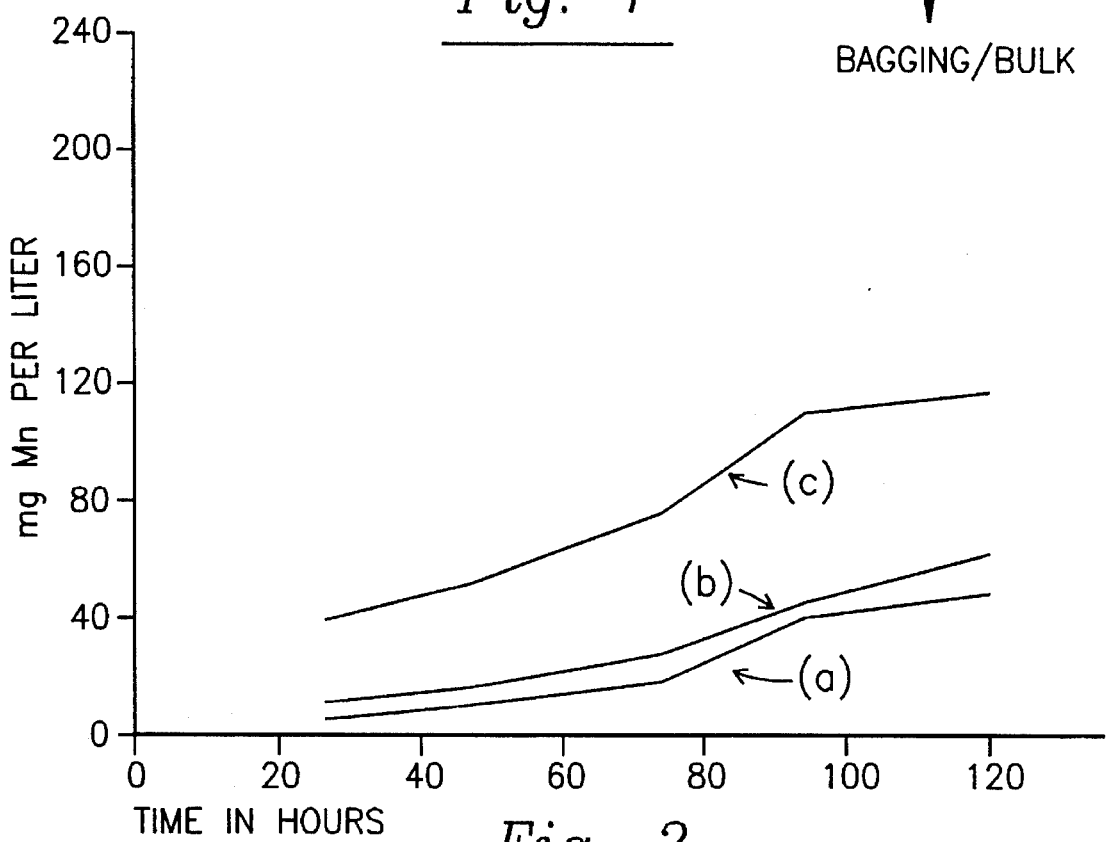
FIG. 2 is a graph showing the difference in plant uptake between prior art nutrient oxides and a nutrient carboxylate (sucrate) of the invention.

Employing AST solution of 21.0 gm sodium bicarbonate, 3.72 gm disodium EDTA, 0.37 gm ammonium fluoride and 0.05 gm superfloc 127 at a pH of 8.93, the solubility of three manganese sources were compared and the results are shown on the graph of FIG. 2. Line (a) was manganous oxide in a saccharide binder sold under the trademark GRANUSOL and made in accordance with the teaching of U.S. Pat. No. 3,567,460. Line (b) was a manganous oxide product and line (c) was the manganese carboxylate (sucrate) employed in this invention in a sugar cane molasses binder. The results show that the manganese carboxylate (sucrate) product solubilizes more rapidly than either of the other products and consequently, is more rapidly taken up by a plant.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. Method of supplying a cationic granular nutrient to a plant in a rapidly solubilizing form comprising applying to an area of plant growth an effective amount of a cationic granular nutrient containing at least 50% dry weight of a salt of saccharic acid of the formula:

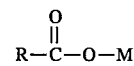

wherein M is a nutrient cation selected from the group consisting of manganese, zinc, copper, iron, magnesium, boron, calcium and potassium and R is a saccharide residue derived from molasses; the cationic granular nutrient being prepared by spraying a stoichiometric excess of a sugar cane molasses containing at least 76% by weight solids on a finely divided powdered oxide having the formula MO wherein M has the same meaning as set forth above; thereafter, drying in a rotary dryer at a temperature of 160° to 175° F. and curing for a sufficient time period to form the cationic granular nutrient.

2. The method according to claim 1 wherein M is manganese.

3. The method according to claim 1 wherein M is zinc.

4. The method according to claim 1 wherein M is copper.

5. The method according to claim 1 wherein M is iron.

6. The method according to claim 1 wherein M is magnesium.

7. The method according to claim 1 wherein M is boron.

8. The method according to claim 1 wherein M is calcium.

9. The method according to claim 1 wherein M is potassium.

10. The method according to claim 1 wherein the cationic granular nutrient is formed by drying in a rotary dryer at about 160° F. while tumbling for 25 to 30 minutes.

11. The method according to claim 1 wherein the cationic granular nutrient is formed by drying in a rotary dryer at about 175° F. while tumbling for 15 to 20 minutes.

\* \* \* \* \*